(12) United States Patent
Riley et al.

(10) Patent No.: US 6,468,564 B1
(45) Date of Patent: *Oct. 22, 2002

(54) TOPICAL COMPOSITIONS CONTAINING LOTUS FOR SKIN TREATMENT

(75) Inventors: Patricia A. Riley, Golden Beach; Thomas Babcock, Hialeah, both of FL (US)

(73) Assignee: Clientele Beauty, Inc., Sunrise, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/953,309

(22) Filed: Sep. 14, 2001

Related U.S. Application Data

(63) Continuation-in-part of application No. 09/327,927, filed on Jun. 8, 1999, now abandoned, which is a continuation-in-part of application No. 08/804,532, filed on Feb. 21, 1997, now abandoned.
(60) Provisional application No. 60/307,758, filed on Jul. 25, 2001.

(51) Int. Cl.$^7$ .............................................. A61K 35/78
(52) U.S. Cl. ........................................ 424/776; 424/725
(58) Field of Search ................................. 424/725, 776

(56) References Cited

FOREIGN PATENT DOCUMENTS

| JP | 4247012 | * | 9/1992 |
| JP | 11071234 | * | 3/1999 |

OTHER PUBLICATIONS

Shen–Miller et al., American Journal of Botany, pp. 1367–1380 (1995).*
MacLaren et al., Protein Express. and Purification 6, pp. 99–108, (1995).*

* cited by examiner

*Primary Examiner*—Jean C. Witz
(74) *Attorney, Agent, or Firm*—Robert E. Pershes

(57) ABSTRACT

Compositions for the treatment of the skin are provided that contain an extract from plants of the genus Nelumbo. These may include the Sacred Lotus (Nelumbo nucifera), the Yellow Lotus (Nelumbo lutea), and the Blue Lotus (Nelumbo caerula). The extract may be from the seed of the plant. The extract is combined with other ingredients to form a suitable formulation for application to the skin. The composition may include other desirable ingredients such as moisturizers and sun screens as well. The composition may be applied to other portions of the integument as well, including the hair and the nails for enhancing the appearance thereof.

14 Claims, 6 Drawing Sheets

NECK/ BEFORE        AFTER

RIGHT HAND/BEFORE        RIGHT HAND/BEFORE
LEFT HAND/AFTER         LEFT HAND/AFTER

BEFORE	AFTER

BEFORE
AFTER
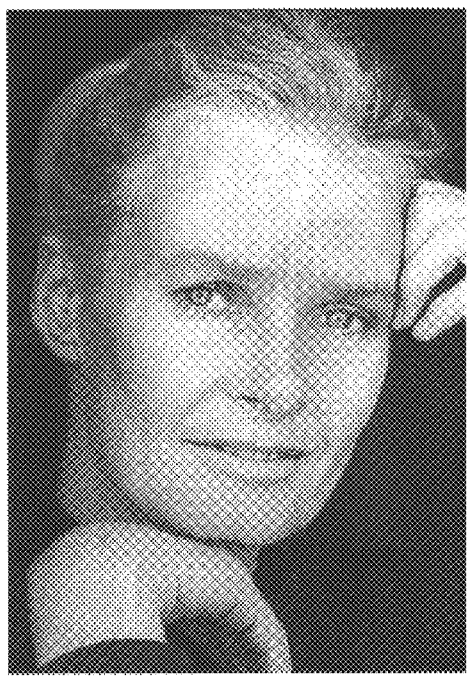
BEFORE
FIG. 3
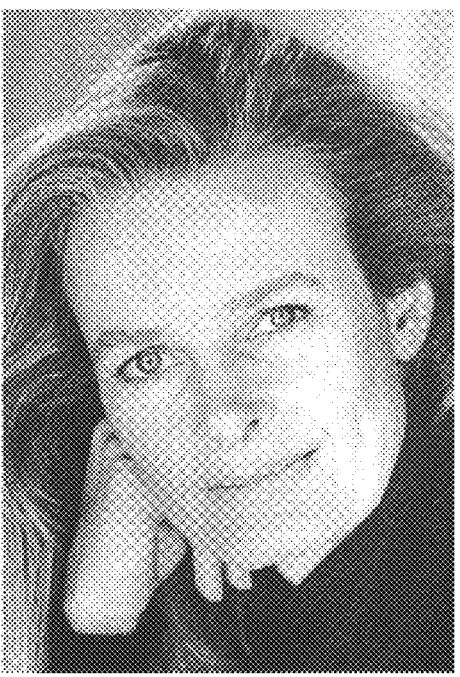
AFTER

BEFORE

AFTER

BEFORE

AFTER

BEFORE

AFTER

BEFORE

AFTER

BEFORE
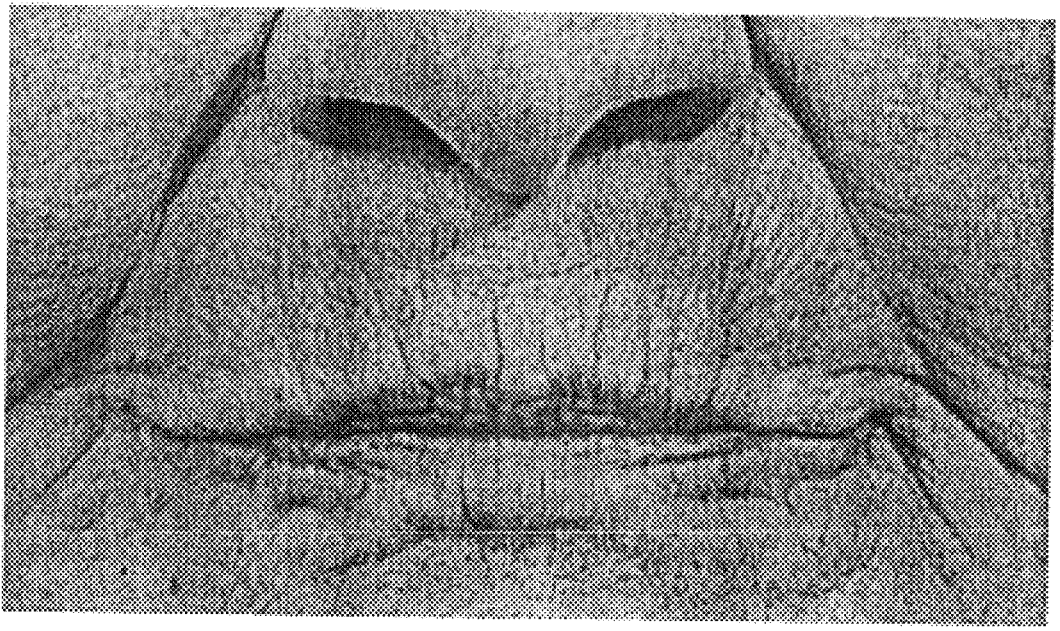
FIG. 6
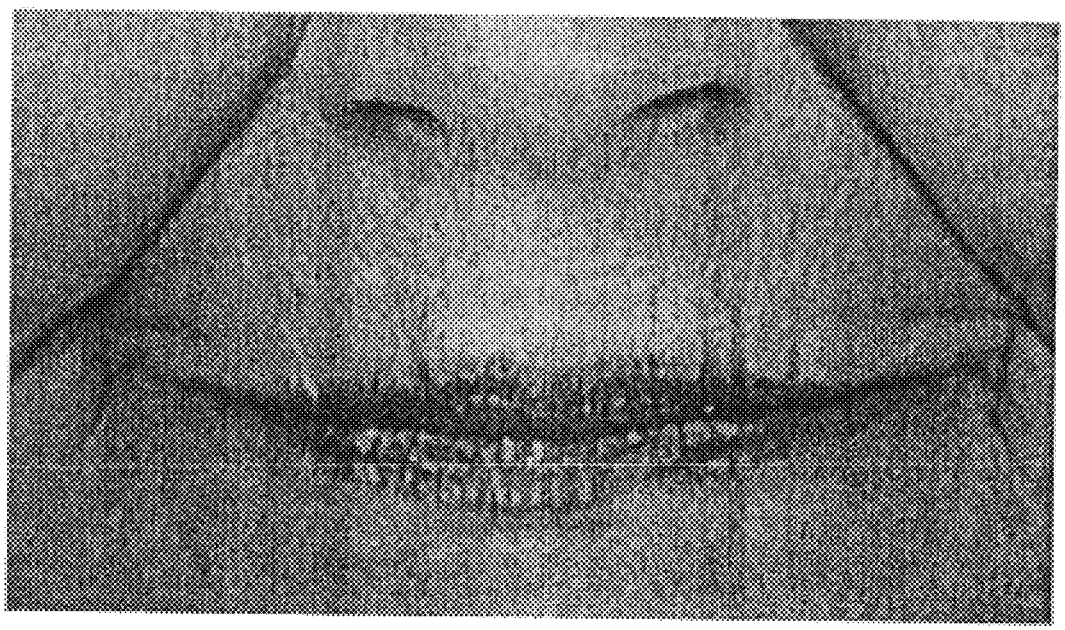
AFTER

TOPICAL COMPOSITIONS CONTAINING LOTUS FOR SKIN TREATMENT

This application is a continuation in part of U.S. patent application Ser. No. 09/327,927, filed Jun. 8, 1999 now abandoned, which is a continuation in part of U.S. patent application Ser. No. 08/804,532 filed Feb. 21, 1997, abandoned. Applicants hereby claim the benefit of provisional patent application Ser. No. 60/307,758 filed Jul. 25, 2001.

FIELD OF THE INVENTION

The present invention relates to the use of the Lotus plant and especially the Lotus seed extract in topical compositions for application to the skin to enhance the appearance thereof.

BACKGROUND

Within the dermis are highly stable fibers of collagen and elastin. Collagen, the most abundant protein in the body, has a high tensile strength thus preventing skin from being torn by over stretching. Elastin, also a protein, allows movement. As skin ages elastic tissue increases but it loses the ability to stretch and recover. This loss of resiliency and elasticity is accompanied by increased stiffness, sagging and wrinkling. Changes in collagen solubility and cross-linking contribute to loss of elasticity.

On the cellular level, aspartyl and isoaspartyl residues are prominent sites of age related damage in proteins. These damaged sites have been characterized in a variety of proteins, but are particularly common in the long-lived proteins. Enzymatic mechanisms for reversing damage to DNA are well established and have been shown to be essential for expanded lifespan.

Experiments performed in vitro with recombinant and chemically modified polypeptides have shown that the presence of an L-isoaspartyl residue may alter both enzymatic activity and the binding of other molecules.

Limiting the accumulation of these residues within cells is currently believed to be important; all human cells examined thus far contain an L-isoaspartyl/D-aspartyl protein methyltransferase that has been proposed to serve this function. It is also believed that this methyltransferase can recognize both D-aspartyl and L-isoaspartyl residues. In addition, it is thought that this enzyme may have the ability to reverse at least part of the damage to protein molecules.

Although the human isoaspartyl protein repair methyltransferase has been purified from red blood cells and had its protein sequence determined, in addition to harvesting a variant in a bacterial system, the availability and use of methyltransferase has been limited.

On or around Nov. 14, 1995, however, it was reported that scientists germinated a 1,288 year old Sacred Lotus seed. The research reported in the November issue of the American Journal of Botany, began in 1982, when Jane Shen-Miller, a plant physiologist at the University of California at Los Angeles (UCLA), obtained seven brown, oval-shaped Sacred Lotus seeds from the Beijing Institute of Botany.

In 1983, Jane Shen-Miller filed through the hard shells of four of the ancient Sacred Lotus seeds and watched three of them sprout. She then dried and burned the seedlings so she could use radiocarbon dating to establish the ages, the oldest of which was 1,288 years old.

According to the November, 1995 report, one of those ancient Sacred Lotus seeds had been in the ground for over 1,200 years; it therefore has been postulated that the Sacred Lotus seeds act as embryos that posses anti-aging properties.

Up until this point, geneticists knew only about proteins that repaired damaged DNA. But findings have suggested that the L-isoaspartyl methyltransferase (MT) enzyme, found in the Sacred Lotus seeds and nearly all other organisms, may have the ability to repair other proteins—those that make up cells and tissues, thus slowing tissue decay.

In these ancient Sacred Lotus seeds, the MT enzyme was present at levels comparable to modern day Sacred Lotus seeds. Damaged proteins did not accumulate within the ancient Sacred Lotus seeds, suggesting that the MT enzyme, possibly along with other constituents, kept the ancient Sacred Lotus seeds alive for so many years.

Notwithstanding the above, it is unknown as to whether use of methyltransferase or extracts or components of the Sacred Lotus plant in topical or oral compositions would be effective in combating aging, repairing damaged skin and/or restoring skin to a more youthful appearance. Moreover, there are no known acceptable products available which incorporate methyltransferase or extracts or components of the Sacred Lotus for combating dermatological aging, repairing damaged skin and/or restoring skin to a more youthful appearance.

Consequently, there exists a need for acceptable delivery systems which incorporate methyltransferase or extracts or components of the Sacred Lotus plant for effectively treating and preventing aging, and repairing damaged skin and restoring skin to a more youthful appearance.

SUMMARY OF THE INVENTION

In brief, the present invention alleviates and overcomes certain of the above mentioned problems and shortcomings of the present state of the art through the discovery of novel acceptable delivery systems which embody methyltransferase or extracts or components of the Sacred Lotus plant for effectively treating and preventing aging, repairing damaged skin and restoring skin to a more youthful appearance and methods of using same.

Accordingly it is the object of the invention to provide a general method for prevention or alleviation of damage to the skin associated with aging through the topical use of methyltransferase in combination with a suitable carrier or vehicle.

Another object is to restore the skin to a more youthful appearance.

Another object is to use the extract of the Sacred Lotus (Nelumbo Nucifera) seed or as a natural source of methyltransferase. It has now been observed, surprisingly and unexpectedly, that by using an extract of the Sacred Lotus seed by topical administration as an active agent, signs of aging can be reduced, eliminated or even reversed.

Another object is to add Sacred Lotus seed extract to existing cosmetic preparations or to use it by itself to reduce the appearances of lines and wrinkles.

Another object is to enhance a cosmetic composition to make the skin appear younger by adding an extract of Lotus seed.

Also until the present invention there were no acceptable vehicles utilizing methyltransferase from a natural source such as lotus seeds and its other natural components in an elegant cosmetic and/or basic pharmaceutical composition and/or dietary formulation. Thus another object of the present invention are formulations of Sacred Lotus seed in dermatologicals, such as lotions, creams, sunscreens, cleansers, and various skin care formulas to improve the youthful appearance of the skin, repair visible damage, and reduce the signs of aging including loss of elasticity, fine lines, wrinkles, blemishes, A suitable carrier or vehicle will include the formulation of creams, gels, lotions, powders, tablets, capsules, and liquid preparations for the skin to repair damage from aging, reduce further damage and restore skin to a more youthful appearance.

These and other objects are achieved by the present invention which is directed to topical formulation for the protection of the skin against damage caused by aging and a method for preventing or alleviating such damage and restoring it to a more youthful appearance by employing such in a topical formulation.

The formulation is a suitable cosmetic or dermatologically acceptable non-toxic, non-allergenic carrier containing methyltransferase and other components of the seed or of the Sacred Lotus plant.

The above features and advantages of the present invention will be better understood with reference to the accompanying FIGS., detailed description and examples. It should also be understood that the particular methods and formulations illustrating the present invention are exemplary only and not to be regarded as limitations of the present invention.

BRIEF DESCRIPTION OF THE FIGS.

Reference is now made to the accompanying FIGS. In which is shown illustrative results of exemplary embodiments of the present invention from which is novel and unique features and advantages will be apparent.

FIG. 3 depicts before and after results on faces following treatment with one of the topical compositions set forth in examples 2–6.

FIG. 6 depicts before and after results on facial skin around the mouth following treatment with one of the topical compositions set forth in examples 2–6.

DETAILED DESCRIPTION

Figure 1:
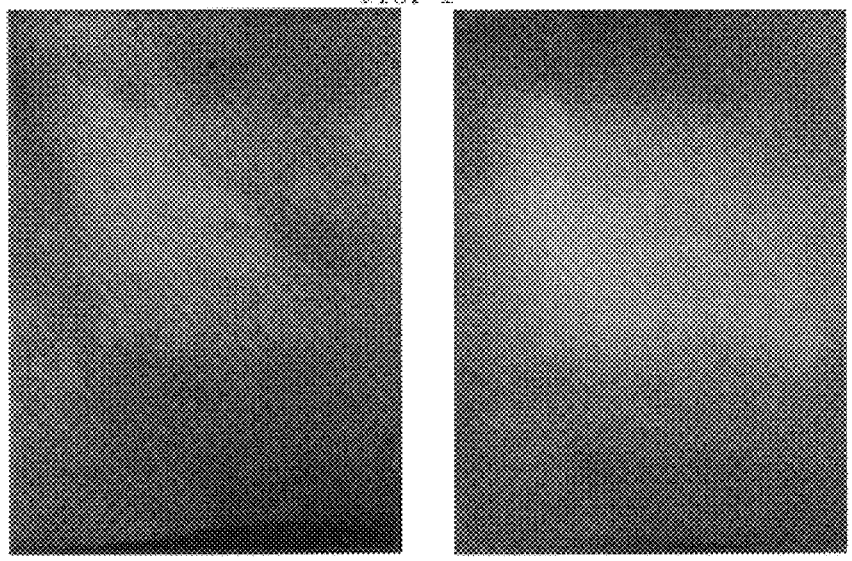
FIG. 1 depicts the left hand of a subject following treatment with a composition as set forth in example 1, and the right hand of the same subject that has received no treatment.
Figure 1:
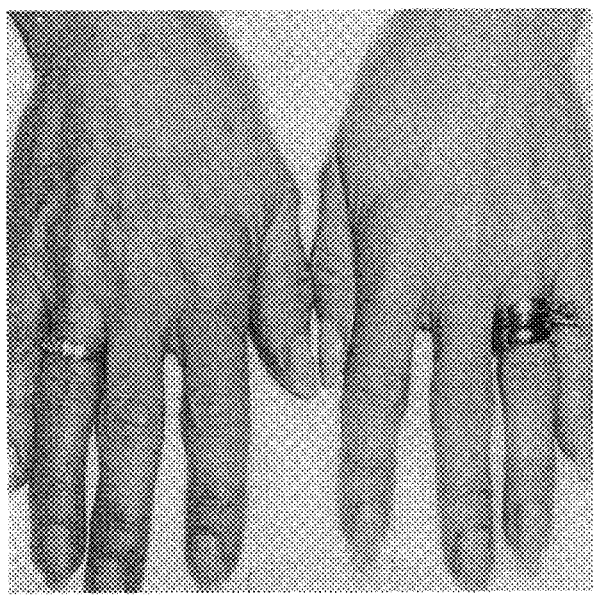
Figure 1:
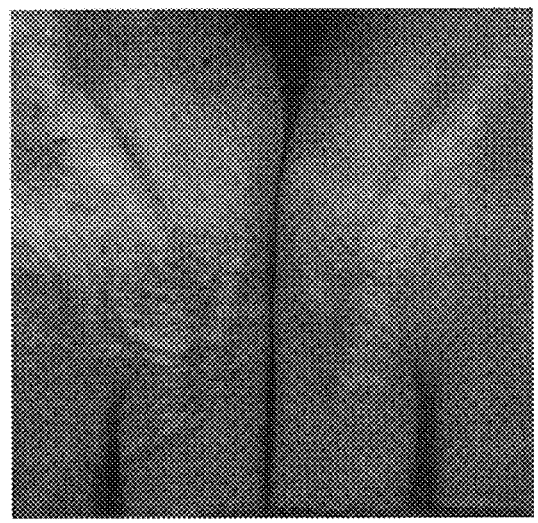

By way of illustrating and providing a more complete appreciation of the present invention and many of the attendant advantages thereof, the following detailed description and examples are given concerning the novel delivery systems which embody methyltransferase or extracts or components of the Sacred Lotus plant for effectively treating and preventing aging, repairing damaged skin and restoring skin to a more youthful appearance and improving overall health and methods of using same.

The present invention uses Sacred Lotus seed extract in skin formulas to combat aging. It is believed that the use of Sacred Lotus seeds in cosmetics accomplish anti-aging effects based on anti-aging factors (enzymes such as methyltransferase) which are present in the seeds.

Moreover, Sacred Lotus seeds contain certain antioxidants such as vitamin C and glutathione which may contribute to anti-aging effects on skin along with methyltransferase and may even contain other beneficial factors.

In accordance with the present invention, methyltransferase and/or the natural compounds found in an extract of Sacred Lotus seeds may be used in an effort to repair age related signs of the skin such as lines, spots, wrinkles, and/or loss of elasticity. Other sources of methyltransferase that may be used in the invention are components of Sacred Lotus plants, extracts of Yellow Lotus seeds or components of Yellow Lotus plants, extracts of Purple Lotus seeds or components of Purple Lotus plants, extracts of Blue Lotus seeds or components of Blue Lotus plants, extracts of other Lotus seeds or components of other Lotus plants where methyltransferase may be present, wheat germ oil, liver, brain, other animal parts including glands, and biofermentation or chemical synthesis for example.

An extract is prepared, for example, as follows. Maceration is the preferred process since no heat is used which may destroy or alter temperature sensitive components; however percolation, digestion, infusion and decoction are within the scope of the invention as more scientific information becomes available.

A twenty percent extract of NELUMBO NUCIFERA is generally used and prepared by placing 200 grams of finely milled untreated whole seeds, including husks and piths, in a stoppered container with about 750 ml of a 50/50 wt/wt mixture of purified water and propylene glycol U.S.P. and allowed to stand for a period of at least 3 days in a warm place with frequent agitation, until soluble matter is dissolved. The mixture is filtered and, after most of the liquid has drained, the residue on the filter is washed with sufficient quantity of the solvent mixture; the filtrates are combined to produce 1000 ml.

It is also within the scope of the present invention to use different amounts of the seed, other parts of the plant as well as other species, solvents and mixtures.

While it is believed that Sacred Lotus "Nelumbo Nucifera" is a preferred species and the seed is a preferred part, other parts of the plant or other species, such as the Yellow Lotus "Nelumbo Lutea", Blue Lotus "Nelumbo Caerulea" containing these "anti-aging" enzymes or constituents are believed to be suitable alternatives for accomplishing the objectives of the present invention.

A composition according to the present invention for topical application contains an effective amount of the anti-aging agent Sacred Lotus seed extract from 0.05% to 100% by weight of the extract relative to the total weight of the composition, and preferably from 0.10% to 10% concentration by weight. It should be understood that the topical compositions may be used at any appropriate daily intervals, depending of course upon the particular type of composition formulated. For instance, the night serum, as set forth in Example 3 hereinafter, is to be administered once-a-day at night after proper cleansing, whereas the wrinkle serum of Example 2 may be administered twice-a-day in the morning and evening. The spot lightening formulation of Example 4, on the otherhand, may be applied, after cleansing, initially on a daily basis for about 6 to 8 weeks, at which time fading will gradually occur. Administration then may be reduced to only 1 to 2 times per week, after cleansing, to prevent reappearance of spots. The wrinkle alpha-hydroxy formulation set forth in Example 6 may be applied once or twice daily following cleansing; however, if dryness occurs, use of this product may be reduced to 1 to 3 times a week.

A composition according to the present invention may be in any of the cosmetic or pharmaceutical forms which are generally used for topical application such as liquids (both aqueous and non-aqueous solutions), creams (both oil-in-water and water-in-oil, O/W & W/O emulsions), gels (both aqueous and non-aqueous), lotions, serums, ointments, paste, powders, liposomes, laminates, microspheres, capsules, and tablets.

Compositions of the present invention may also contain additives such as water, alcohols, oils(mineral vegetable, animal and synthetics), glycols, colorants, preservatives, emulsifiers, gelling agents, gums, esters, hormones, steroids, antioxidants, silicones, polymers, fragrances, flavors, sunscreens, other active ingredients, acids, bases, buffers, vitamins, minerals, salts, polyols, proteins and their derivative essential oils, other enzymes, co-enzymes and extracts, surfactants, detergents, soaps, anionics, non-ionics, ionics, waxes, lipids, UV filters, stabilizers, fillers, celluloses, glycans, amines, solubilizers, thickeners, sugars and sugar derivatives, ceramides, sweeteners and the like, so long as such additives do not defeat the objectives of the present invention.

A composition according to the present invention as an effective anti-aging agent may be employed alone, that is without the use of additional actives, or the Sacred Lotus seed may be used to enhance other ingredients.

One preferred composition combines the Sacred Lotus seed with glucosamine, hyaluronic acid, and alpha hydroxy acids for their role in glycosaminoglycan (a protein sugar complex essential for normal hydration in the skin) synthesis plus antioxidants such as vitamins A, C, E, and extracts of pine bark, grape seed and green tea, catalase, superoxide dismutase and coenzyme Q-10 to protect the skin from free radicals and alleviate further cellular damage.

Other items such as lecithin, squalene, panthenol, vitamin D3, jojoba oil, olive oil, glycerin and other moisturizers also appear to benefit with the addition of Sacred Lotus seed in providing moisture into the skin enhancing its repair process, promoting elasticity and making the skin appear younger.

Hydroquinone, sulfur and salicylic acid also appear to exhibit synergism with Sacred Lotus Seed extract.

The following examples are given for illustrative purposes only to delineate some of the features of the invention and are not intended to be limiting. As to exemplary formulations set forth below, the quantities are given in approximate weight (% wt) or approximate units (I.U.) unless otherwise noted based on the total weight of the composition. The term qs means to use a sufficient quantity by weight to bring the entire composition to 100%. Whenever possible International Nomenclature Cosmetic Ingredient (INCI) names are used.

EXAMPLE 1

| Anti-Aging Moisture Concentrate | |
|---|---|
| Part I: | |
| Water | 78.10 |
| Diazolidinyl Urea | 0.30 |
| Methylparaben | 0.20 |
| Part II: | |
| Hydroxyethylcellulose | 0.30 |
| Stearamidopropyl Dimethylamine Lactate | 1.50 |

| -continued | |
|---|---|
| Anti-Aging Moisture Concentrate | |
| Glycerin | 2.00 |
| Cetyl Alcohol | 4.00 |
| Glycol Stearate | 3.50 |
| Propylparaben | 0.10 |
| Part III: | |
| Sacred Lotus Seed Extract | 10.00 |

Procedure:

Part I is mixed and heated to 80 C. Part II is slowly added with mixing; then covered and with continued mixing the heat is removed and cooling started. At 40 C, Part III is added. At 35 C mixing is stopped.

A thick luscious fat and oil free lotion was obtained to moisturize aged and dried skin.

EXAMPLE 2

| Anti-Aging Wrinkle Serum | |
|---|---|
| Part I: | |
| Water | 75.36 |
| Glycerin | 1.50 |
| Tetrasodium EDTA | 0.10 |
| Panthenol | 0.30 |
| Diazolidinyl Urea | 0.30 |
| Methylparaben | 0.25 |
| Sodium PCA | 0.50 |
| Part II: | |
| Magnesium Aluminum Silicate | 0.90 |
| Part III: | |
| Glyceryl Dilaurate | 0.50 |
| Sunflower Oil | 10.00 |
| Olive Oil | 2.50 |
| Cetyl Alcohol | 2.70 |
| Glyceryl Stearate PEG-100 | 3.00 |
| Propylparaben | 0.10 |
| Part IV: | |
| Tocopheryl Acetate | 0.50 |
| Retinyl Palimate | 0.05 |
| Coenzyme Q-10 | 0.01 |
| Part V: | |
| Corn oil, Glyceryl Oleate, Propylene Glycol, BHA, BHT, Propyl Gallate, & Citric Acid | 0.05 |
| Magnesium Ascorbyl Phosphate | 0.05 |
| Catalase | 0.25 |
| Superoxide Dismutase | 0.25 |
| Beta Carotene | 0.01 |
| Green Tea Extract | 0.10 |
| Grape Seed Extract | 0.10 |
| Pine Bark Extract | 0.10 |
| Sacred Lotus Seed Extract | 0.20 |
| 25% Sodium Hydroxide qs to pH 7.00 | 0.20 |
| Fragrance | 0.30 |

Procedure:

Part I is mixed and heated to 80 C. Part H is slowly added with mixing; then covered and continued mixing for 30 minutes. Part III is mixed and heated also to 80 C. Part III is then added to Parts I and II with mixing. With continued mixing the heat is removed and cooling started. At 50 C Part IV is added. At 40 C Part V is added followed by fragrance. At 35 C mixing is stopped. PH is measured and adjusted if necessary.

An enriched serum that readily dispenses from a pump to alleviate wrinkles.

EXAMPLE 3

Anti-Aging Night Serum For Dry Skin

Part I

| | |
|---|---|
| Water | 51.62 |
| Glycerin | 2.00 |
| Tetrasodium EDTA | 0.05 |
| Panthenol | 1.50 |
| Diazolidinyl Urea | 0.20 |
| Methylparaben | 0.20 |

Part II:

| | |
|---|---|
| Hydroxyethylcellulose | 0.10 |

Part III:

| | |
|---|---|
| Propylene Glycol | 3.00 |
| Cetearyl Phosphate | 1.00 |
| Cetearyl Alcohol | 1.00 |
| DEA Cetyl Phosphate | 2.20 |
| Cetyl Alcohol | 2.00 |
| Glycol Stearate | 1.00 |
| Soybean Oil | 3.00 |
| Propylparaben | 0.10 |
| Squalene | 3.00 |
| Polysorbate 20 | 0.40 |
| Jojoba Oil | 2.00 |
| Cyclomethicone | 2.00 |
| Phenyl Dimethicone | 3.00 |
| Titanium Dioxide | 1.00 |

Part IV

| | |
|---|---|
| Tocopheryl Acetate | 1.50 |
| Coenzyme Q-10 | 0.01 |
| Retinyl Palmitate | 0.20 |

Part V

| | |
|---|---|
| Oat Beta Glucan | 1.00 |
| Magnesium Ascorbyl Phosphate | 0.30 |
| Catalase | 1.00 |
| Superoxide Dismutase | 2.00 |
| Beta Carotene | 0.05 |
| Green Tea Extract | 1.00 |
| Grape Seed Extract | 1.00 |
| Pine Bark Extract | 1.00 |
| Sacred Lotus Seed Extract | 4.00 |
| N-Acetyl Glycosamine | 2.00 |
| Saccharide Isomerate | 2.00 |
| Sodium Hyaluronate | 2.00 |
| Histidine HCL | 0.50 |
| 25% Sodium Hydroxide qs to pH 7.00 | 0.02 |
| Fragrance | 0.25 |

Procedure:

Part I is mixed and heated to 80 C. Part II is slowly added with mixing; then covered and continued mixing for 30 minutes. Part III is mixed and heated also to 80 C. Part m is then added to Parts I & II with mixing. With continued mixing the heat is removed and cooling started. At 50 C Part IV is added. At 40 C Part V is added followed by fragrance. At 35 C mixing is stopped. PH is measured and adjusted if necessary.

A serum that is used at night to restore moisture to dry skin.

EXAMPLE 4

Anti-Aging Spot Lightener

Part I:

| | |
|---|---|
| Water | 91.79 |
| Hydroquinone | 2.00 |
| Ascorbic Acid | 1.00 |
| Sodium Metabisulfite | 0.15 |
| Diazolidinyl Urea | 0.30 |
| Methylparaben | 0.20 |
| N-Acetyl Glucosamine | 1.00 |
| Citric Acid | 0.10 |

Part II

| | |
|---|---|
| Polysorbate 20 | 2.00 |
| Fragrance | 0.20 |
| 25% Sodium Hydroxide qs to pH 5.50 | 0.26 |
| Sacred Lotus Seed Extract | 1.00 |

Procedure:

Part I is mixed until completely clear. Adjust pH of Part I to 5.50+/−0.10 with 25% Sodium Hydroxide solution. Premix Part II and add slowly to Part I with constant mixing. When clear, the Sacred Lotus Seed Extract is added and stirred until completely clear.

A thin solution that is easily used from a roll-on applicator to target age spots, freckles, uneven skin tone and damage caused by the sun.

EXAMPLE 5

Anti-Aging Acne Blemish Treatment

Part I

| | |
|---|---|
| SD Alcohol 40-B | 67.85 |
| Salicylic Acid | 2.00 |
| Sacred Lotus Seed Extract | 1.00 |
| Witch Hazel Distillate | 10.00 |
| Glycerin | 10.00 |

Part II

| | |
|---|---|
| Retinyl Palmitate | 0.05 |
| Fragrance | 0.10 |
| Polysorbate 20 | 10.00 |

Procedure:

Mix Part I until completely clear keeping covered to avoid any alcohol loss. Mix Part II until uniform. Add Part II to Part I and mix until clear.

A simple topical that is effective especially on oily skin without excessive irritation.

EXAMPLE 6

Anti-Aging Alpha Hydroxy Acid Wrinkle Treatment

Part I

| | |
|---|---|
| Water | 76.61 |
| N-Acetyl Glucosamine | 1.00 |
| Aloe (10X conc.) | 0.20 |
| Magnesium Ascorbyl Phosphate | 0.50 |
| Diazolidinyl Urea | 0.20 |
| Methylparaben | 0.10 |

-continued

| Anti-Aging Alpha Hydroxy Acid Wrinkle Treatment | |
|---|---|
| Part II | |
| Glycolic Acid 70% | 7.14 |
| Blackcurrent Extract, Bilberry Extract, Citric Acid, Glycolic Acid, Lactic Acid & Malic Acid. | 1.00 |
| Sugar Cane Extract, Citric Acid, Glycolic Acid, Lactic Acid, and Malic Acid | 1.00 |
| Part III: | |
| Polysorbate 20 | 1.50 |
| Retinyl Palmitate | 0.05 |
| Fragrance | 0.20 |
| Tocopheryl Acetate | 0.50 |
| 25% Sodium Hydroxide qs to pH 5.00 | 8.00 |
| Sacred Lotus Seed Extract | 2.00 |

Procedure:

Part I is mixed until completely clear. Part II is also mixed until completely clear. Part II is added to Part I and mixed until clear. Adjust pH of Parts I and II to 5.00 with 25% Sodium Hydroxide solution. Premixed Part III is added and mixed until clear followed by Sacred Lotus Seed Extract addition.

A liquid combination of various alpha hydroxy acids with Sacred Lotus Seed Extract shown to be effective in reducing the appearance of lines and wrinkles. Also minimized pore size and improved the texture of the skin imparting a more youthful and radiant appearance.

EXAMPLE 7

During the course of a Dermatologist's clinical study it was discovered that a lotion containing Sacred Lotus extract alone resulted in a decrease in the appearance of aging sun-damaged skin on the hands. The lotion used in this example 7 was the Anti-Aging Moisture Concentrate set forth in Example 1 above. In two participants, the Lotus Seed extract alone was used in a 10% concentration with either a placebo or active formulated lotion on the hands.

Side by side comparison of the treated vs. untreated hand of one participant showed obvious differences. The skin of the treated hand was more porcelain in appearance, there was reduction in fine wrinkling, dryness and the hand appeared less aged and less sun-damaged. In another participant, one hand was treated, and before and after photographs showed similar results. See FIG. 1.

EXAMPLE 8

Figure 2:
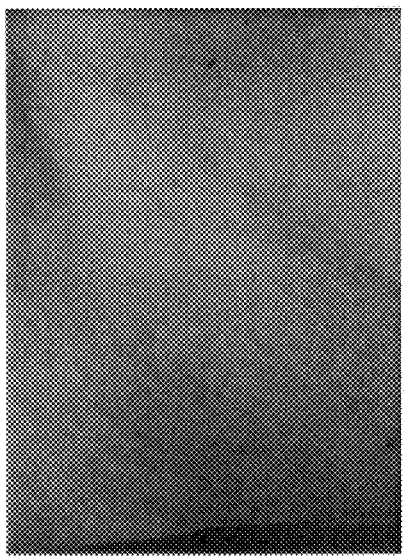
FIG. 2 depicts before and after results on a neck following treatment with a composition as set forth in example 1.
Figure 2:
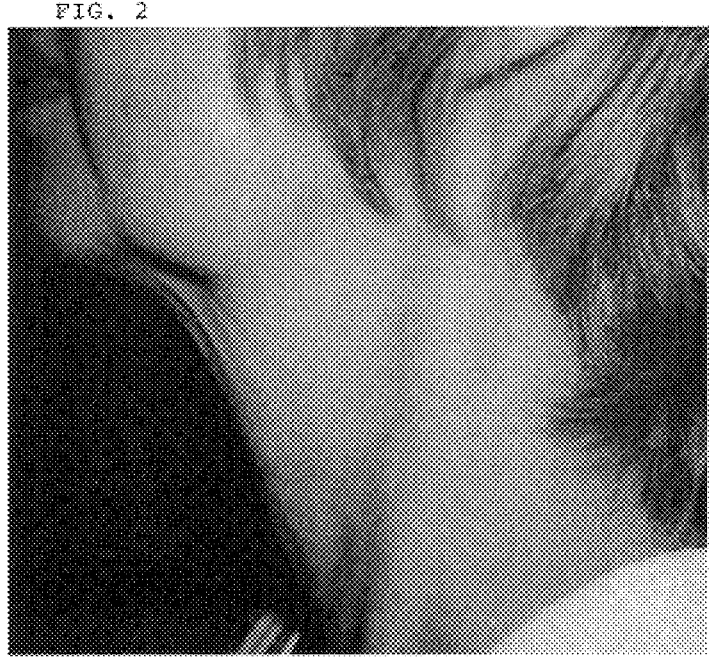
Figure 2:
Figure 2:
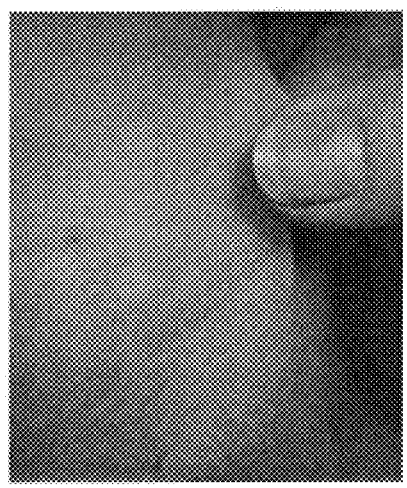
Figure 4:
FIG. 4 depicts before and after results on faces following treatment with one of the topical compositions set forth in examples 2–6.
Figure 4:
Figure 4:
Figure 4:
Figure 5:
FIG. 5 depicts before and after results on facial skin around the eyes following treatment with one of the topical compositions set forth in examples 2–6.
Figure 5:
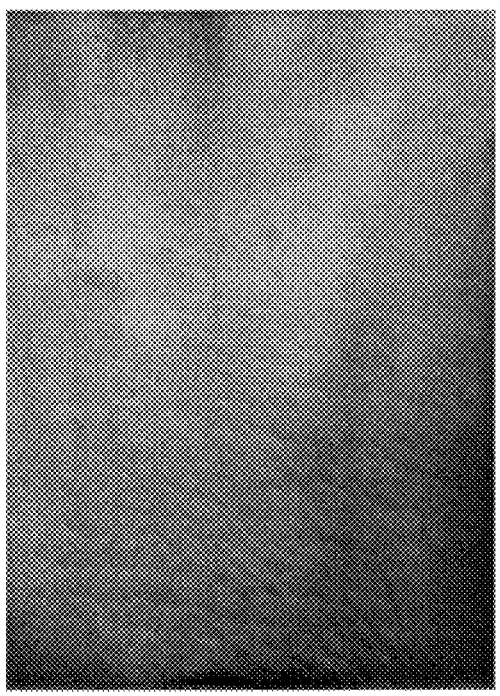
Figure 5:
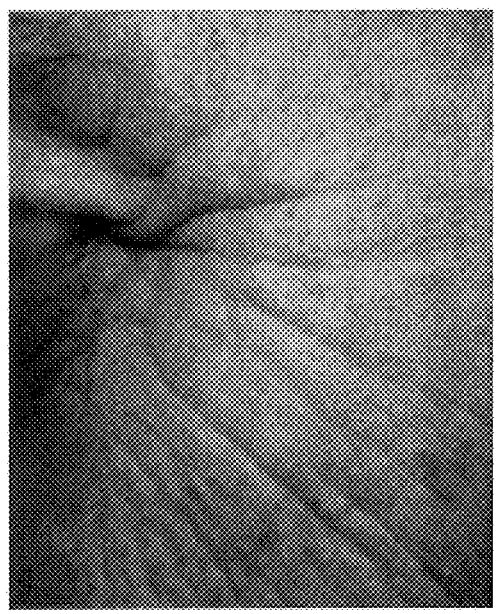
Figure 5:

In another study using the Anti-Aging Moisture Concentrate set forth in Example 1 above, the neck of one patient showed dramatic results, according to side by side comparisons of treated vs. untreated skin of the neck. The patient then went on to treat the untreated side, which was the left side, and this also showed the dramatic improvement seen on the previously treated right side. See FIG. 2.

There was also unexplained improvement in the elasticity in a right to left comparison. See FIG. 2 which are photographs that were taken of a pinch test of the skin. On the treated right side of the neck, pinching of the skin revealed very little and difficulty in pinching up any loose skin, and the untreated left side of the neck, skin was easily pinched up to a much greater degree and the skin fold was larger.

EXAMPLE 9

In order to test the effectiveness of the Sacred Lotus Seed Extract when combined with other ingredients another study was done. Two different groups were given the various formulations containing Sacred Lotus Seed Extract, as set forth in Examples 2–6 set forth above to use for twelve weeks. The first panel consisted of eight professional models. The second used fourteen women employed in other occupations. See tables 3 and 4 respectively.

The Dermatologist noted dramatic improvements in the patients using the formulas containing Sacred Lotus Seed Extract. The formulas increased elasticity, reduced visible pore size, promoted a more refined skin texture, reduced the appearance of crow's feet, lines and wrinkles, reduces blemishes, lightened dark spots promoted firmer, younger looking skin. See FIGS. 3, 4, 5 and 6.

The left column lists the various categories sought to be improved, for example brown spots, blemishes, smaller pores, etc. The next columns give the results of the panel members. The last column is the average percent improvement of the responses given in each category. The top row identifies the participant by number. The bottom row gives overall result of the improvement. Some items are blank because no improvement was needed in that particular category.

An additional study was then performed employing the composition of Example 1. This was a more objective study whose results are shown in tables 1 and 2, and is described as follows:

12 people were entered into a double blind placebo controlled study for the evaluation of lotus extract on human skin. Six participants were evaluated for the Lotus effect on the appearance of wrinkles and 6 participants were evaluated for the effect of the Lotus extract on pore size and acne. One person dropped out of the wrinkle study due to time constraints and one person dropped out of the pore study for personal reasons.

The data presented in this report summarizes the data collected on the participants completing the wrinkle study. Four females and one male with ages ranging from 35 to 65 years completed 4 weeks of treatment.

Statistical Analysis of Method 1

The severity of wrinkling was observed to decline from 5.38 to 2.4 after 4 weeks of treatment. This change was statistically significant (ANOVA, p=0.00006). Treatment with a placebo resulted in no significant change in severity (3.92 initial reading and 3.44 after 4 weeks; ANOVA, p=0.34).

Statistical Analysis of Method 2

Assessment of the percent reduction in wrinkles also revealed a significant decline as compared to treatment with a placebo (ANOVA. p=0.000009).

Results and Conclusions:

Lotus extract led lo a reduction in the appearance of wrinkles. Using the Method 1 analysis in which the evaluators graded the wrinkles on a 0 to 10 scale (with 10 being the worst), the analysis of silflo silicon replicas revealed that there was a 51.6% reduction in the appearance of wrinkles in the active agent group versus a 12.24% improvement with the placebo lotion. The analysis of clinical photographs revealed that there was a 57.86% reduction in the appearance of wrinkles after 4i weeks of treatment Using the method 2 analysis, in which the evaluators compared the before and after silflo replicas of active agent and placebo treated subjects in a blinded fashion and directly estimated the percent wrinkle reduction by visual assessment, there was a 42.8% percent reduction in the appearance of wrinkles when treated with the lotus extract, but only a 10.4% improvement in the placebo treated areas. The analysis of the clinical photographs also showed a 42.72% reduction in the appearance of wrinkles when the before and after photographs were directly compared.

The composition of the invention may also be provided with extracts of plant material from members of the Lotus genus (Nelumbo) not specifically described herein for enhancing the appearance of the integument of the user. The integument of the user may include the hair, the skin and the nails.

While we have shown and described the preferred embodiments of our invention, it will be understood that the invention may be embodied otherwise than as herein specifically illustrated or described, and that certain changes in form and arrangement of components and the specific manner of practicing the invention may be made within the underlying idea or principles of the invention.

TABLE 1

Method 1 DATA
Wrinkle Score on a 0 to 10 scale at week 0 and week 4

| | Active wk 0 | active wk 4 | placebo wk 0 | placebo wk 4 | clinical week 0 | clinical wk 4 | clinical wk 0 | clinical wk 4 |
|---|---|---|---|---|---|---|---|---|
| Patient 1 | | | | | site 1 | site 1 | site 2 | site 2 |
| | 3.00 | 1.00 | 3.00 | 3.00 | 3.00 | 1.00 | | |
| | 7.00 | 6.00 | 7.00 | 5.00 | 7.00 | 3.00 | | |
| | 6.00 | 3.00 | 4.00 | 4.00 | 7.00 | 3.00 | | |
| | 2.00 | 1.00 | 4.00 | 6.00 | 8.00 | 2.00 | | |
| | 6.00 | 2.00 | 6.00 | 7.00 | 7.00 | 2.00 | | |
| subtotal | 24.00 | 13.00 | 24.00 | 25.00 | 32.00 | 11.00 | | |
| Patient 2 | | | | | site 2 | site 2 | site 3 | site 3 |
| | 7.00 | 2.00 | 1.00 | 1.00 | 8.00 | 1.00 | | |
| | 5.00 | 2.00 | 2.00 | 1.00 | 5.00 | 1.00 | | |
| | 6.00 | 2.00 | 6.00 | 3.00 | 5.00 | 2.00 | | |
| | 5.00 | 3.00 | 4.00 | 4.00 | 6.00 | 4.00 | | |
| | 2.00 | 2.00 | 2.00 | 2.00 | 2.00 | 2.00 | | |
| subtotal | 25.00 | 11.00 | 15.00 | 11.00 | 26.00 | 10.00 | | |
| Patient 3 | | | | | site 3 | site 3 | site 4 | site 4 |
| | 3.00 | 2.00 | 2.00 | 1.00 | 5.00 | 3.00 | 5.00 | 1.00 |
| | 9.00 | 4.00 | 6.00 | 8.00 | 9.00 | 4.00 | 8.00 | 3.00 |
| | 5.00 | 5.00 | 2.00 | 2.00 | 7.00 | 5.00 | 6.00 | 3.00 |
| | 8.00 | 3.00 | 7.00 | 5.00 | 6.00 | 3.00 | 10.00 | 2.00 |
| | 8.00 | 4.00 | 3.00 | 4.00 | 9.00 | 3.00 | 6.00 | 3.00 |
| subtotal | 33.00 | 18.00 | 20.00 | 18.00 | 36.00 | 18.00 | 35.00 | 12.00 |
| Patient 4 | | | | | site 4 | site 4 | site 5 | site 5 |
| | 4.00 | 1.00 | 1.00 | 1.00 | 5.00 | 2.00 | 6.00 | 3.00 |
| | 6.00 | 2.00 | 6.00 | 6.00 | 8.00 | 4.00 | 8.00 | 4.00 |
| | 5.00 | 3.00 | 4.00 | 3.00 | 4.00 | 2.00 | 4.00 | 3.00 |
| | 4.00 | 2.00 | 4.00 | 4.00 | 5.00 | 3.00 | 6.00 | 2.00 |
| | 3.00 | 1.00 | 1.00 | 1.00 | 3.00 | 1.00 | 3.00 | 1.00 |
| subtotal | 22.00 | 9.00 | 16.00 | 15.00 | 25.00 | 12.00 | 27.00 | 13.00 |
| Patient 5 | | | | | site 5 | site 5 | site 6 | site 6 |
| | 2.00 | 1.00 | 3.00 | 2.00 | 2.00 | 1.00 | | |
| | 7.00 | 3.00 | 7.00 | 6.00 | 5.00 | 2.00 | | |
| | 4.00 | 2.00 | 4.00 | 2.00 | 4.00 | 2.00 | | |
| | 7.00 | 4.00 | 8.00 | 6.00 | 2.00 | 1.00 | | |
| | 2.00 | 0.00 | 1.00 | 1.00 | 3.00 | 1.00 | | |
| subtotal | 22.00 | 10.00 | 23.00 | 17.00 | 16.00 | 7.00 | | |
| patient totals | 126.00 | 61.00 | 98.00 | 86.00 | 197.00 | 83.00 | | |
| | n = 25 | n = 25 | n = 25 | n = 25 | n = 35 | n = 35 | | |
| Wrinkle reduction with the week 0 value normalized to 100 | 100.00 | 48.42 | 100.00 | 87.76 | 100.00 | 42.14 | | |
| Percent improvement | | 51.60 | | 12.24 | | 57.86 | | |

TABLE 2

Method 2 DATA
Percent reduction in the appearance of wrinkles

|  | Active | Placebo | clinical assessment | clinical assessment site 2 |
|---|---|---|---|---|
| Patient 1 | 50.00 | 0.00 | 65.00 | |
|  | 50.00 | 20.00 | 60.00 | |
|  | 40.00 | 0.00 | 40.00 | |
|  | 50.00 | 0.00 | 60.00 | |
|  | 20.00 | 30.00 | 50.00 | |
| subtotal | 210.00 | 50.00 | 275.00 | |
| Patient 2 | 20.00 | 0.00 | 40.00 | |
|  | 0.00 | 0.00 | 0.00 | |
|  | 50.00 | 50.00 | 50.00 | |
|  | 30.00 | 50.00 | 40.00 | |
|  | 30.00 | 5.00 | 50.00 | |
| subtotal | 130.00 | 105.00 | 180.00 | |
| Patient 3 | 40.00 | 10.00 | 50.00 | 30.00 |
|  | 50.00 | 20.00 | 30.00 | 80.00 |
|  | 0.00 | 0.00 | 30.00 | 30.00 |
|  | 30.00 | 10.00 | 30.00 | 60.00 |
|  | 60.00 | −10.00 | 60.00 | 70.00 |
| subtotal | 180.00 | 30.00 | 200.00 | 270.00 |
| Patient 4 | 50.00 | 0.00 | 30.00 | 60.00 |
|  | 40.00 | 0.00 | 40.00 | 50.00 |
|  | 10.00 | 5.00 | 20.00 | 20.00 |
|  | 40.00 | 0.00 | 50.00 | 50.00 |
|  | 50.00 | 0.00 | 40.00 | 50.00 |
| subtotal | 190.00 | 5.00 | 180.00 | 230.00 |
| Patient 5 | 30.00 | 0.00 | 20.00 | |
|  | 30.00 | 20.00 | 50.00 | |
|  | 30.00 | 10.00 | 20.00 | |
|  | 20.00 | 20.00 | 10.00 | |
|  | 60.00 | 20.00 | 60.00 | |
| subtotal | 170.00 | 70.00 | 160.00 | |
| Grand total | 1,070.00 | 260.00 | 1,495.00 | |
|  | n = 25 | n = 25 | n = 35 | |
| Average % improvement | 42.80 | 10.40 | 42.72 | |

TABLE 3

| IMPROVEMENT | 1 | 2 | 3 | 4 | 5 | 6 | 7 | 8 | AVERAGE % |
|---|---|---|---|---|---|---|---|---|---|
| BROWN SPOTS | 80 |  | 90 | 100 | 90 | 80 | 100 | 70 | 87.10% |
| LESS BLEMISHES | 80 |  | 90 | 70 | 90 | 90 | 100 | 100 | 88.60% |
| SMALLER PORES | 100 | 90 | 90 | 80 | 80 | 90 | 100 | 100 | 91.30% |
| MOUTH WRINKLES | 80 |  | 90 | 100 | 90 | 80 | 100 | 80 | 88.60% |
| CROWS FEET | 80 | 100 | 100 | 80 | 80 | 80 | 100 | 90 | 88.60% |
| LINES FOREHEAD | 80 | 80 | 90 | 90 | 80 | 80 | 100 | 90 | 86.30% |
| TEXTURE | 90 |  | 90 | 100 | 100 | 100 | 100 | 100 | 97.10% |
| MOISTURE | 90 |  | 90 | 100 | 70 | 90 | 100 | 80 | 88.60% |
| SMOOTHER SOFTER | 90 | 100 | 90 | 100 | 100 | 100 | 100 | 100 | 97.50% |
| LESS ROUGHNESS | 80 | 100 | 90 | 100 | 100 | 80 | 100 | 100 | 93.80% |
| RADIANCE | 90 | 100 | 100 | 100 | 100 | 100 | 100 | 90 | 97.50% |
| YOUNGER LOOKING | 80 | 100 | 100 | 100 | 100 | 100 | 100 | 90 | 96.30% |
| DIFFERENCES | 100 | 90 | 90 | 100 | 100 | 90 | 100 | 100 | 96.30% |

TABLE 4

| IMPROVEMENT | 1 | 2 | 3 | 4 | 5 | 6 | 7 | 8 | 9 | 10 | 11 | 12 | 13 | 14 | AVERAGE % |
|---|---|---|---|---|---|---|---|---|---|---|---|---|---|---|---|
| BROWN SPOTS | 80 | 100 | 80 | 90 | 80 | 90 | 100 | 90 | 70 | 70 | 90 | 90 | 70 |  | 84.60% |
| LESS BLEMISHES | 80 | 100 | 70 | 70 | 90 | 90 | 100 | 80 | 90 | 70 | 70 | 80 | 100 |  | 83.80% |
| SMALLER PORES | 80 | 100 | 80 | 90 | 90 | 90 | 100 | 90 | 90 | 90 | 90 | 100 | 100 |  | 91.50% |
| MOUTH WRINKLES | 90 | 100 | 80 | 90 | 90 |  |  | 70 | 70 | 90 | 100 | 90 | 90 |  | 87.30% |
| CROWS FEET |  | 100 | 80 | 90 | 90 |  |  | 70 | 70 | 90 | 90 | 90 | 100 |  | 87.00% |
| LINES FOREHEAD | 80 | 100 | 80 | 90 | 90 | 90 |  | 80 | 70 | 90 | 90 | 90 | 90 |  | 86.70% |
| TEXTURE | 90 | 100 | 90 | 100 | 100 | 90 |  | 100 | 90 | 90 | 90 | 80 | 100 | 100 | 93.80% |
| MOISTURE | 100 | 100 | 90 | 90 | 90 | 90 |  | 90 | 100 | 90 | 100 | 80 | 100 | 100 | 93.80% |
| SMOOTHER SOFTER | 100 | 100 | 90 | 90 | 90 | 90 | 100 | 100 | 100 | 100 | 90 | 80 | 100 | 100 | 95.00% |
| LESS ROUGHNESS | 100 | 100 | 80 | 90 | 90 | 90 |  | 100 | 90 | 100 | 90 | 80 | 100 | 100 | 92.30% |
| RADIANCE | 90 | 100 | 80 | 100 | 100 | 90 | 100 | 100 | 90 | 100 | 100 | 90 | 100 | 100 | 95.70% |
| YOUNGER LOOKING | 80 | 100 | 90 | 90 | 90 | 90 |  | 100 | 100 | 90 | 100 | 90 | 100 | 100 | 93.80% |
| OVERALL DIFFERENCES | 90 | 100 | 90 | 100 | 100 | 90 | 100 | 100 | 90 | 90 | 100 | 90 | 100 | 100 | 95.70% |

What is claimed is:

1. A topical composition for application to the skin, said topical composition comprising:
   a) an extract of the seed of plant material selected from the group consisting of the Yellow Lotus (Nelumbo lutea), the Blue Lotus (Nelumbo caerulea) and the Sacred Lotus (Nelumbo nucifera); and
   b) a compatible vehicle for topical application.

2. The topical composition according to claim 1 in which said extract of the seed of plant material is from the Sacred Lotus (Nelumbo nucifera).

3. The topical composition according to claim 1 in which said extract of the seed of plant material is from the Yellow Lotus (Nelumbo lutea).

4. The topical composition according to claim 1 in which said extract of the seed of plant material is from the Blue Lotus (Nelumbo caerulea).

5. The topical composition according to claim 1 further comprising a moisturizing agent.

6. The topical composition according to claim 1 further comprising a sun screen agent.

7. The topical composition according to claim 6 further comprising a moisturizing agent.

8. A topical composition for application to the integument to enhance the appearance thereof, said topical composition comprising:
   a) an extract of the seed of plant material selected from the group consisting of the Yellow Lotus (Nelumbo lutea), the Blue Lotus (Nelumbo caerulea), and the Sacred Lotus (Nelumbo nucifera); and
   b) a compatible vehicle for topical application.

9. The topical composition according to claim 8 in which said extract of the seed of plant material is from the Sacred Lotus (Nelumbo nucifera).

10. The topical composition according to claim 8 in which said extract of the seed of plant material is from the Yellow Lotus (Nelumbo lutea).

11. The topical composition according to claim 8 in which said extract of the seed of plant material is from the Blue Lotus (Nelumbo caerulea).

12. The topical composition according to claim 8 further comprising a moisturizing agent.

13. The topical composition according to claim 8 further comprising a sun screen agent.

14. The topical composition according to claim 13 further comprising a moisturizing agent.

* * * * *